United States Patent [19]

Taylor

[11] Patent Number: 4,696,025
[45] Date of Patent: Sep. 22, 1987

[54] SCANNING APPARATUS

[75] Inventor: Kenneth W. Taylor, Mississauga, Canada

[73] Assignee: University of Toronto Innovations Foundation, Toronto, Canada

[21] Appl. No.: 870,316

[22] Filed: Jun. 2, 1986

[51] Int. Cl.4 ............................................. G21K 5/10
[52] U.S. Cl. ................................... 378/146; 378/181; 378/177
[58] Field of Search .............. 378/146, 167, 177, 181, 378/195, 196, 197, 198, 208, 209

[56] References Cited

U.S. PATENT DOCUMENTS

| | | | |
|---|---|---|---|
| 2,496,089 | 1/1950 | Goldfield et al. | 378/177 |
| 3,150,260 | 9/1964 | Smith | 378/177 |
| 4,404,591 | 9/1983 | Bonar | 378/146 |

Primary Examiner—Janice A. Howell
Assistant Examiner—David P. Porta
Attorney, Agent, or Firm—Thomas A. O'Rourke

[57] ABSTRACT

Apparatus are disclosed to scan an elongate portion of the patient. The apparatus have a low power x-ray source and imaging assembly, each having a collimating slit through which an x-ray beam is transmitted. Means are provided to move the patient relative to the x-ray source. A film pack is located in the imaging assembly and is mounted on a motor carrier to move the film pack progressively past the slit axis so as to record the image obtained. The low power x-ray beam is offset by a high speed film and an image intensifier in the imaging assembly, thereby reducing the amount of radiation subjected on the patient.

11 Claims, 6 Drawing Figures

SCANNING APPARATUS

The present invention relates to radiological examination apparatus and in particular to apparatus that may be used to scan a portion of a body.

The use of X-rays to obtain an image of internal portions of the body is of course well known. It is also known to obtain information about an elongate area of a body such as the spine or a bone in the leg by scanning that particular area of the body. This is usually achieved by irradiating the body through a collimating slit and recording the image on a film located behind an imaging slit that moves in union with the collimating slit. The slits move progressively along the body and expose successive portions of the film.

This technique requires the use of a film having an overall size corresponding to the length of the structure to be examined. This in turn requires the body to be exposed to standard relatively large doses of radiation and if it is required to examine the structure over an extended period of time the accumulated exposure to radiation may become hazardous. Therefore the technique is not used as often as may be desired.

It is therefore an object of the present invention to obviate or mitigate the above disadvantages.

According therefore to the present invention there is provided radiological examination apparatus comprising:

a source of radiation to irradiate a body to be examined;

imaging means to receive radiation from said source after transmission through said body and provide an image thereof;

support means to connect said source and said imaging means to maintain alignment therebetween whilst permitting relative movement between said imaging means and said body along a predetermined path to provide a scan of a portion of said body;

recording means to record the image provided by said imaging means during said scan, said recording means being moveable along said path relative to said imaging means, and motion control means acting on said recording means to maintain relative movement between said body and said imaging means in a predetermined ratio to movement between said imaging means and said recording means, whereby the length of the image recorded on said recording means is less than the relative displacement between said imaging means and said body.

Embodiments of the invention will now be described, by way of example only with reference to the accompanying drawings in which.

Figure 1:
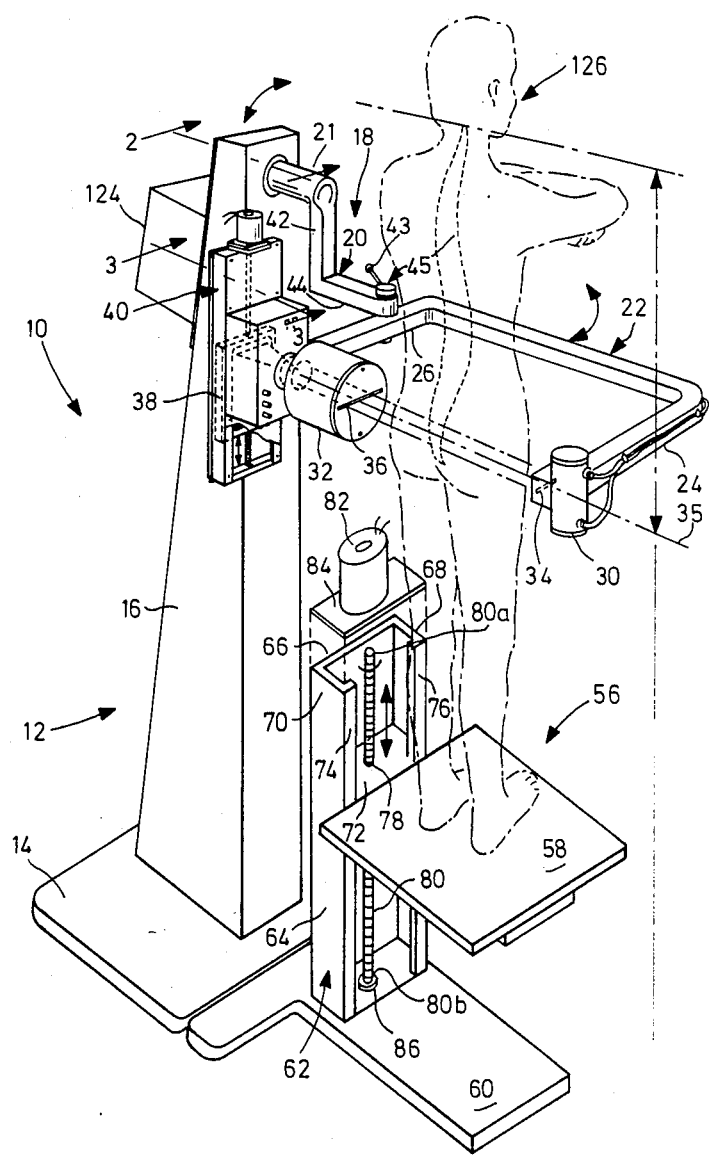
FIG. 1 is a general perspective view of a radiological examination apparatus showing a patient positioned to conduct a scan of the spine.

With reference to FIG. 1, a radiological examination apparatus generally designated 10 comprises a support structure 12 having a horizontal base 14 and a vertical support 16. Pivotally coupled to vertical support 16 is a frame 18, having an angular arm 20, one end of which is fixed to a rotatable cylindrical boss 21, while the other end is pivotally connected with a bracket 22. The bracket 22 has two substantially parallel arms 24 and 26, which respectively position an x-ray source 30 and an imaging assembly 32.

Collimating slits 34, 36 of the source 30 and imaging assembly 32 respectively, are maintained in constant alignment by the bracket 22 which allows accurate collection of transmitted x-rays by a film pack 38 located in the rear portion of the imaging assembly 32. The x-ray source generates a low power x-ray beam which is compensated by the use of a high speed film, having a film speed of 3000 ASA. The film pack 38 is moveable along a motorized carrier 40 to enable the film pack to scan progressively the x-ray signal entering the slit 36. Positioned beneath the frame 18 is an elevating device 56 having a platform 58 which is moveable relative to base 60 by way of a lift assembly 62.

Motion of the working components of the apparatus is made possible in three distinct locations on the apparatus 10 to assist in obtaining a small image of a larger scanning area with corresponding low dosage. Briefly stated, motion may occur by: rotation of the frame 18 relative to the support structure 12 via cylindrical boss 21; reciprocation of the film pack 38 relative to the imaging assembly 32 via carrier 40 and reciprocation of the platform 58 relative to the base 60 via lift assembly 62. Dynamic areas are hereinafter described with reference to FIGS. 1-5.

Figure 2:
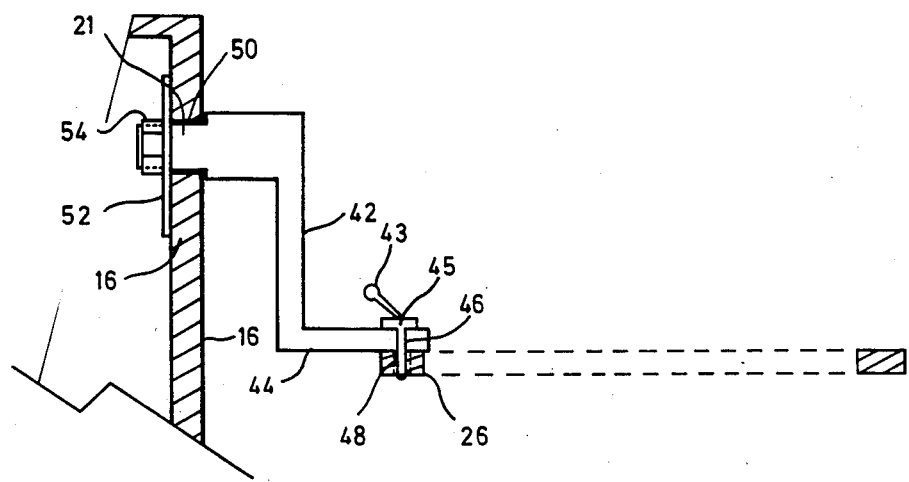
FIG. 2 is a partly sectional fragmented side view taken along line 2—2 of FIG. 1.
Figure 3:
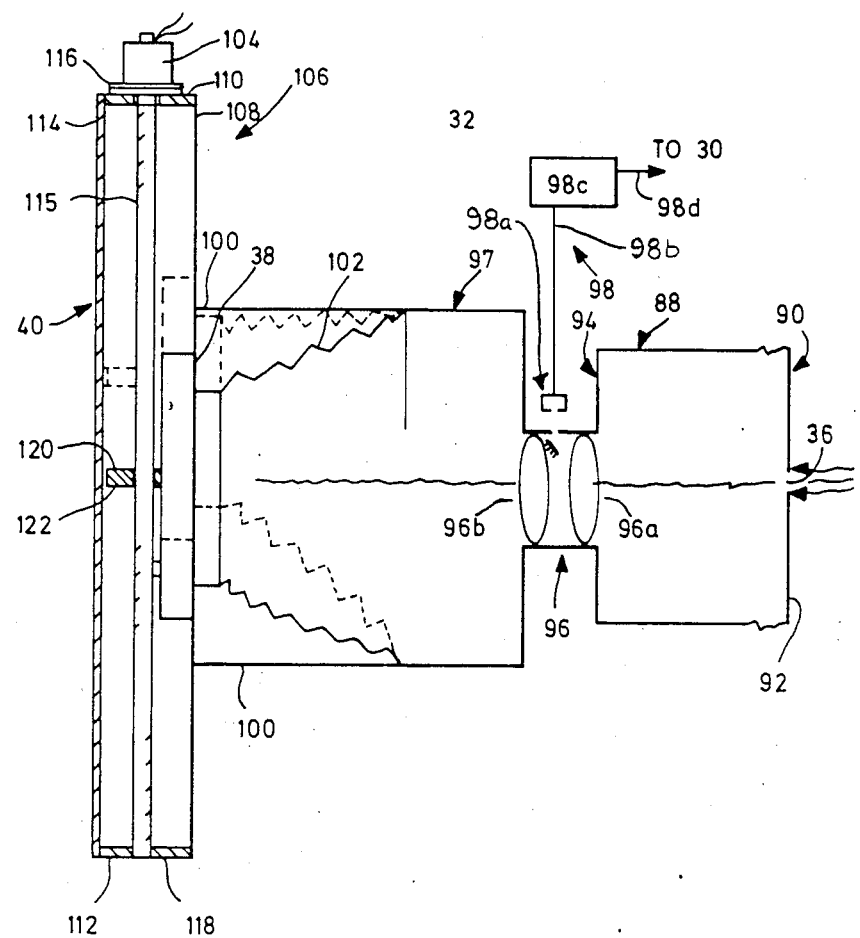
FIG. 3 is a sectional side view taken along line 3—3 of FIG. 1.

To orient the x-ray source 30 and the imaging means 32 in operational position about the area to be scanned, the rotatable mounting of the frame 18 to the vertical support 16 is employed. As is shown in FIG. 2, this is accomplished with cylindrical boss 21, which is joined to one end of a vertical portion 42 of angular arm 20.

Joined to the other end of vertical portion 42 is horizontal portion 44 whose free end is pivotally connected to bracket 22, via a pivot pin 45. Pivot pin 45 passes through bores 46 and 48 of horizontal portion 44 and arm 26 respectively as shown in FIG. 2. Bore 48 is also threaded for engagement with pivot pin 45. Boss 21 extends through a bore 50 formed in vertical support 16 and rotatably retained therein by way of washer 52 and nut 54 threaded on the rearwardly emerging end of boss 21.

The rotatable connection of the frame 18 on vertical support 16 enables the x-ray source and imaging assembly to be positioned about the patient in a lying position on a gurney 19, as will be described with reference to FIG. 4. In this case, the frame 18 is swung to rotate about the boss 21 and held in position until bolt 54 is tightened, securing the arm in proper orientation, i.e. with the area of interest positioned within the bight of support 46.

Figure 4:
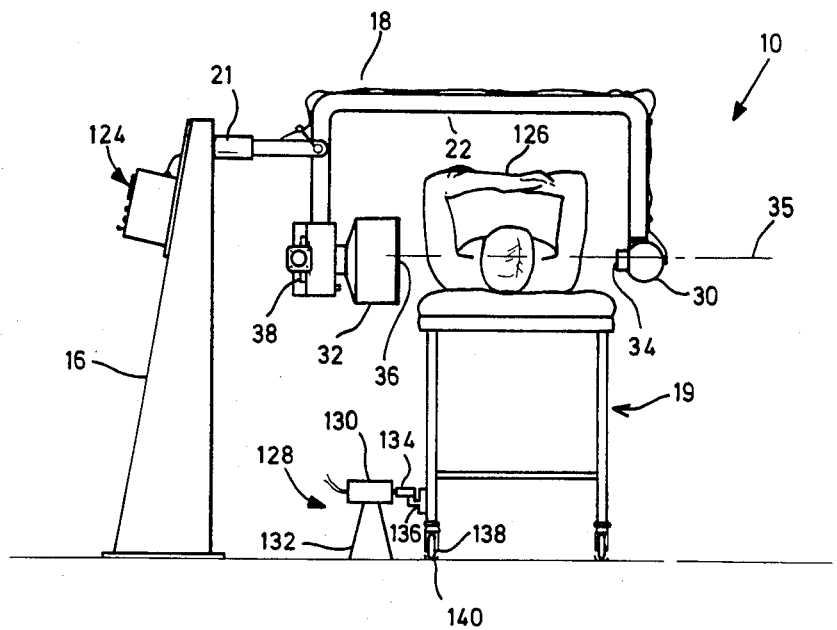
FIG. 4 is a view similar to FIG. 1 showing an alternative method of obtaining a scan of the spine with a portion of the apparatus in FIG. 1.

Rotation of the bracket 22 about the boss 21 thus allows the operational components to be positioned in a desired orientation about the patient whether the patient is standing, as shown in FIG. 1 or alternatively in a horizontal position a gurney 19, shown in FIG. 4.

A further motion originates from the pivotal connection of the bracket 22 to the horizontal portion 44 member, which is provided by pivot 45. The pivot 45 includes a crank 43 enabling bracket 22 to be fixed in any given position relative to horizontal portion 44.

Finally, reciprocation of the platform 58 relative to the base 60 of elevating device 56 is provided by lift assembly 62 which comprises a rectangular channel member 64 defined by back wall 66 and side walls 68, 70. A slider block 72 is constrained for displacement along the inner surface of walls 66, 68 and 70 by flanges 74, 76 inwardly extending from side walls 68 and 70 respectively. Slider block 72 is further defined by a centrally disposed threaded bore 78 through which extends a lead screw 80. Coupled to the upper end 80a of lead screw 80 is lift motor 82 which is positioned on channel member 64 by a holding plate 84. The lower end 80b of screw 80 is engaged with bushing 86 which is mounted on base 60.

When scanning of a desired area is effected, x-rays are caused to emanate from x-ray source through collimating slit 34, impinge on the image intensifiers and are selectively transmitted therethrough. To provide for a continuous recording medium onto which transmitted rays may be recorded, controlled displacement of film pack 66 relative to the collimator slit 59 is provided, as hereinafter described with reference to FIG. 3.

The imaging assembly 32 inlcudes an image intensifier 88 having an input face 90. Lead collimator 92 bearing slit 36 is mounted on the input face 90 that is directed towards the x-ray source. The output face 94 of the image intensifier 88 is connected to a camera lens carried by a camera body 97. Lens assembly 96 includes a pair of lenses 96a and 96b. Located between the lenses is a mirror 96c which reflects a small portion of the image to an intensity control unit 98. The camera body 98 is formed with a pair of rear extensions 100 that act as supports and guideways for a film pack 38. The film pack 38 is connected to the camera body 98 via bellows 102 which permits relative movement between the film pack 38 and camera body 98. The extensions 100 guide the film pack 38 for movement generally transversely to the focal axis of the camera lens 96 while maintaining it in the imaging plane.

Accordingly, the transmitted rays are collected at collimator 92 of image intensifier 88 where they are converted to a visible minified light image which appears at intensifier output 94. This light image is transmitted through lens assembly 96, camera body 98 and bellows 102, to ultimately impinge on film pack 38 where they are recorded.

The intensity control unit 98 receives a portion of the light image at a photomultiplier 98a which generates a voltage signal proportioned to the amount of light received. This signal is conveyed via conductor 98b to circuit 98c which in turn conveys a feedback signal to x-ray source 30 via conductor 98d. The intensity control unit 98 thereby provides a constant amount of light generated by image intensifier 32 by controlling the intensity of x-rays emitted from x-ray source 30. This ensures a substantially constant density across the recorded image, to offset variations in the thickness of the body being scanned.

Movement of the film pack 38 is provided by motorized carrier 40 having a motor 104 which is mounted on carrier assembly 106. The carrier assembly 106 includes a carrier frame 108 formed from top and bottom panels 110, 112 to which is attached back panel 114. A lead screw 115 extends through bores 116, 118 in top and bottom panels 110, 112 respectively, with the upper end of the lead screw 115 coupled to motor 104. The motor drives lead screw 115 which passes through a threaded bore 120 in a bracket 122 attached to the film pack 38. The lead screw 115 is arranged to drive the film pack 38 in the same direction as the direction in which lead screw 80 lifts platform 58 but at a predetermined speed ratio to enable the film to be exposed progressively. Thus, with the film pack 38 and the platform 58 positioned adjacent the constant speed motors 104, 82 they will travel in a manner which will allow the entire scanned area to be recorded on a film of distinctly smaller area. The image provided on the film in the film pack 66 corresponds to that portion of the object being scanned by the source but on a smaller scale.

Thus, during initial set up of the apparatus the film pack 38 must be positioned at the opposite end of the lead screw 115 as the slider block 72 is positioned on the lead screw 80. Control of the scanning procedure is implemented by way of a control panel 124 located on vertical support 16, which carries a plurality of switching elements to effect manual and automatic displacement of motors 82 and 104, as well as to energize x-ray source 30.

In preparing the apparatus as shown in FIG. 1, for an x-ray scan, the patient identified at 126 is located on platform 58 in a standing position. The motor 82 is first manually energized via control panel 124 to adjust the distance between platform 58 and the axis of the collimating slits 34, 36, as is numerically identified at 35. This enables the lowermost portion of the spine to be aligned with the axis.

The control panel 124 is then activated to initiate the scan, during which the motors 82, 104 respectively displace the platform 58 and the film pack 38 in concert and at a predetermined displacement ratio, which depends on the length of the region of the patent to be scanned, and the length of the film pack 38. At the onset of the movement of platform 58 and film pack 38, the x-ray source 30 is energized to 100 kv at 7 mA so as to generate low power x-rays which travel through the patient 126 and impinge upon the input face 90 of the image intensifier 88.

As is usual, the x-ray intensity reaching the image intensifier face 92 will vary in accordance with the absorption characteristics of the tissues through which the x-rays pass. The image intensifier converts the x-ray image to a visible image bright enough to expose the photographic film. The visible image is then recorded by the film in film pack 38.

Thus, as the patient moves downwardly through the axis of the slits 32, 34, the film moves past the image formed by the camera so that undeveloped film is progressively exposed by the image, to yield a print of the scanning region, having a reduced size commensurate with the magnification rate of the camera lens 96 and the displacement ratio between the motors 82, 104.

When the scan is completed, the film is removed from the film pack 38, which initiates the development of the film to provide a processed print of the radiographic image. The print is typically 100 mm×70 mm. The physician or health professional inspects the photograph which is of sufficient clarity and resolution to facilitate rapid and accurate diagnosis of abnormalities in bones or to establish the present of x-ray opaque foreign bodies. However, the dosage required to obtain such an image is in the order of 1/100th of the dosage usually delivered with full size screens and film combinations.

The film used in the film pack 38 has a nominal speed of 3000 ASA although other speeds could be used. It has been found that 12,000 ASA film also available from the Polaroid Corporation produces an extremely contracted image that is generally unsatisfactory. Similarly lower speeds may be used, for example, 300-600 ASA, but the dosage of radiation will increase to higher levels. However, the advantage of an instant record is retained.

With the 3000 ASA film that has been used the dosage has been reduced to 1/50th to 1/100th of the conventional screen and film techniques, that is an improvement of a factor of 10 over the previous techniques using an image intensifier. Using the 3000 ASA film it has been found that exposures in the range 0.1 mR up to 2.0 mR with a typical general purpose exposure of 1.0 mR can be used to obtain a satisfactory image.

It should be noted that a certain degree of Quantum mottling will be evident upon inspection of the recorded image, and is caused by the small number of x-rays being utilized during the scan. The Quantum mottling anticipated with a higher speed imaging system has been found to be acceptable whilst the benefits of lower dosage have been obtained. Detrimental effects of the mottling are offset in part by the minified image and by the selection of a low contrast film.

The contrast $\delta$ of the film is 1.5 compared with a range of 2.5 to 4.0 for conventional screen and film techniques.

An alternative embodiment is illustrated in FIG. 4 wherein the patient 126 is scanned whilst in a lying position. In this case, the frame is oriented about vertical support 16 such that arms 24 and 26 are in a substantially vertical orientation. Supporting the patient is a gurney 19 which is located between bracket 22 and aligns the spine of the patient with the axis 35 of the colliminating slits 34, 36.

Displacement of the patient relative to the axis 35 is afforded by a displacement assembly 128 involving a motor 130 on a frame 132. The shaft of motor 130 drives a gear 134 which engages with a toothed rail 136 longitudinally disposed along the gurney 19. To maintain proper alignment of the toothed rail 136 with the gear 134, the gurney is equipped with wheels 138 which travel along guide rails 140. The motor 130 is coupled with the control panel 124 for control of motor 130 during a scan procedure.

In order to scan a region of a patient in a lying position the embodiment illustrated in FIG. 4 is employed by adjusting the apparatus as seen. In this case, the frame 18 is rotated about vertical support 16, via boss 21, such that the arms 24, 26 vertically oriented.

The patient is then placed on gurney 19 which is wheeled between the arms 24, 26 of the bracket 22. The gurney 19 positions the patient at a height corresponding to the axis 35 of the colliminating slits.

In preparing for the scan, the gurney is first adjusted with respect to axis 35 so that one end of the patients spine may be aligned with the axis 35. When the alignment is made, the control panel 124 is activated to simultaneously displace the film pack 38 in imaging assembly 32 and gurney 19 in the same direction and at a controlled speed ratio depending on the length of the scanning region of the patient 126 and the length of the film.

Upon displacement of the gurney 19 and the film pack 38, the x-ray source 30 is energized by the control panel 124 to generate a low power x-ray signal as in the previous embodiment.

Figure 5:
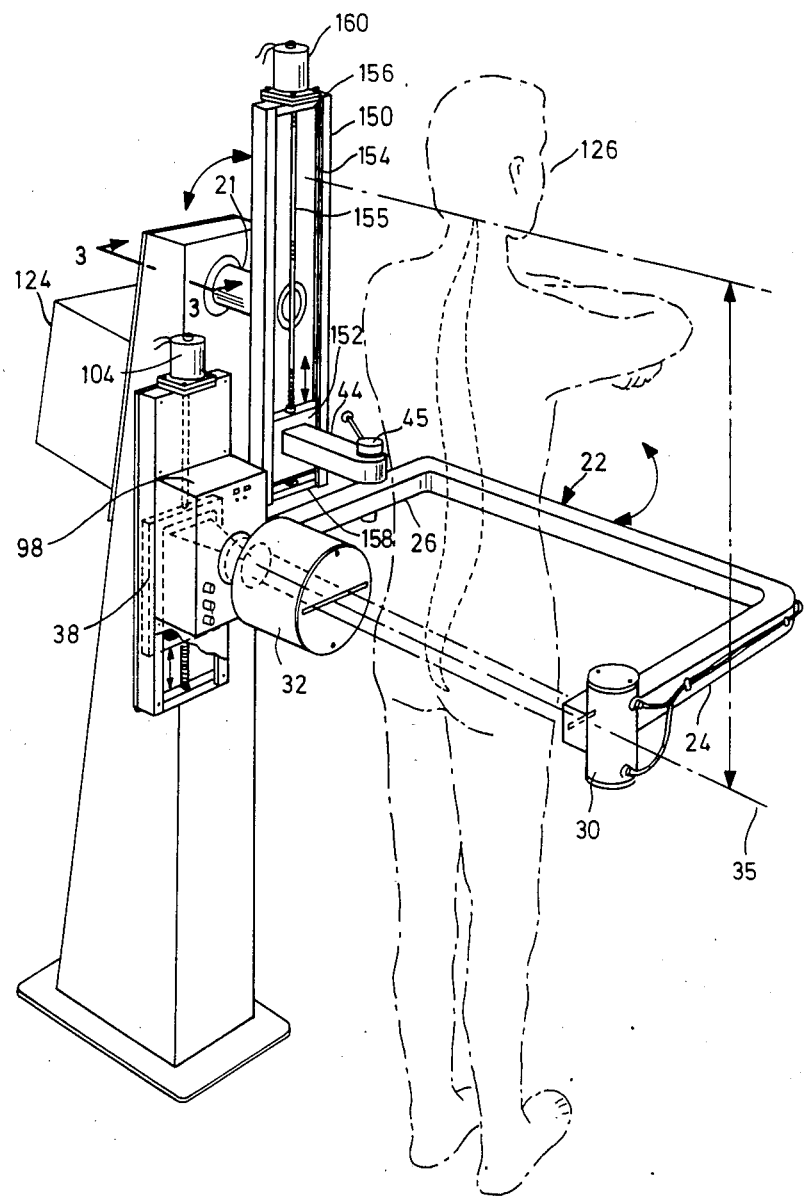
FIG. 5 is a perspective view showing an alternative embodiment of the apparatus shown in FIG. 1.

In yet a further embodiment, as is shown in FIG. 5 the bracket 22 is moveable relative to cylindrical boss 21 to effect a relative displacement of axis 35 relative to the patient 126. In this case, a single carrier 150 is fixably mounted to cylindrical boss 21 and slidably engages a slide member 152.

Scanning is achieved by moving the slide member 152 along a path within the slide carrier 150. Motion of the slide member is translated into motion of the bracket 22 by virture of connection thereof with the slide member 152 via horizontal portion 44. Slide member 152 is held within carrier 150 by grooves 154 of dove-tail cross-section which cooperate with corresponding formations on slide member 152. A lead screw 155 extends along the slide carrier 150 and is supported at opposite ends by brackets 156, 158 respectively. A motor 160 is mounted upon bracket 156 and is connected to the lead screw 155 for rotation thereof relative to the brackets 156, 158. Motor 160 is also coupled with control panel 124 for actuation of the motor during the scanning procedure.

Slide member 152 is further provided with a threaded bore which receives the lead screw 155. In this way rotation of the lead screw 155 by the motor 160 causes controlled displacement of the slide member 152 along the groove 154 resulting in unified movement of the x-ray source 30 and the imaging assembly 32.

To operate the embodiment illustrated in FIG. 5, the patient 126 is positioned between the arms 24, 26 such that the axis is aligned with the spine of the patient. Motor 160 is then actuated via control panel 124 to adjust the height of the bracket 22 such that the axis 35 is at a height corresponding to the lowermost portion of the spine. Adjustments of the orientation of the source 30 and imaging assembly in the plane of axis 35 are also provided by pivot pin 45. In addition, film pack 38 is displaced by way of motor, to the starting position at the lowermost end of camera 98.

With all adjustments made, motors 160 and 104 are simultaneously actuated, which respectively displace the axis 35 and the film pack 38 at a predetermined speed ratio, again dependent on the length of the region to be scanned and the length of the film pack 38.

Thus, it will be noted that the distance travelled by collimating slit 34 of the image intensifier during scanning exceeds the length of the film contained by film pack 38 thereby providing a substantially reduced visual record, in relation to the size of the region scanned.

Figure 6:
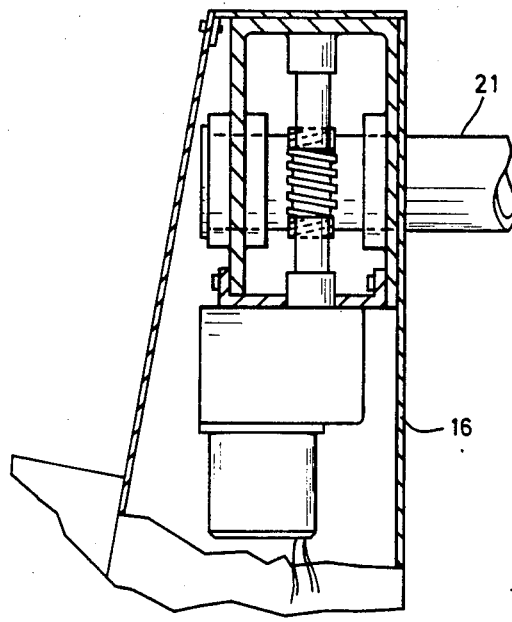
FIG. 6 is a sectional view illustrating another embodiment of the apparatus shown in FIG. 1.

Various alternatives are contemplated for the above described embodiments, including the use of a motor and worm gear arrangement as shown in FIG. 6, to drive cylindrical boss 21.

The apparatus may also be used to obtain a scan of a curved object. In this case the object is rotated about the x-ray source 30 while the film pack 38 is oriented for displacement in the transverse to the axis of rotation.

It should also be noted that the provision of movement of the film pack 38 in concert with that of the patient or bracket is made on the basis that lens 96 presents a non-inverted image on the film pack. Accordingly, use of an inverting lens, the film pack 38 is moved in a direction opposite to that of the patient of the bracket.

The facility to obtain a smaller image of the scanned object enables an x-ray dosage to be used which is substantially lower than with conventional techniques.

Typically reductions in the order of 100 times may be obtained with the result of increased safety.

I claim:

1. Radiological examination apparatus comprising a source of radiation to irradiate a body to be examined;

imaging means to receive radiation from said source after transmission through said body and provide an image thereof;

support means to connect said source and said imaging means to maintain alignment therebetween whilst permitting relative movement between said imaging means and said body along a predetermined path to provide a scan of an enlongate portion of said body;

recording means to record the image provided by said imaging means during said scan, said recording means being moveable along said path with said imaging means, and motion control means acting on said recording means to maintain movement thereof in a predetermined ratio to movement of said imaging means relative to said body whereby the length of the image on said recording means is less than the distance moved by said imaging means relative to said body.

2. Apparatus according to claim 1 wherein said recording means is mounted on said imaging means and said motion control means acts to move said recording means relative to said imaging means.

3. Apparatus according to claim 2 wherein said motion control means is connected to said support means and said motion control means acts between said support means and said recording means to move said recording means in the same direction as said imaging means and at a lesser rate.

4. Apparatus according to claim 1, further comprising body displacement means to displace said body relative to said imaging means so as to provide a relative movement between said imaging means and said body.

5. Apparatus according to claim 1, wherein said support maintains said imaging means in a fixed position in relation to the axis of displacement of said body.

6. Apparatus according to claim 1, wherein said support means displaced said imaging and source means so as to provide said relative movement between said imaging means and said body.

7. Apparatus according to claim 6 wherein said support means includes a base and a slide member moveable relative to said base, said source and imaging means being mounted on said slide member for conjoint translation relative to said body.

8. Apparatus according to claim 4, wherein said body displacement means comprises an elevating means for vertical displacement of said body relative to said imaging means.

9. Apparatus according to claim 8, wherein said elevating means includes a platform on which said body is located, a base and a lift means to displace vertically said platform relative to said base.

10. Apparatus according to claim 4, wherein said body displacement means includes carrying means to translate said body in a horizontal orientation relative to said imaging means.

11. Apparatus according to claim 10, wherein said carrying means includes a gurney device on which said body is placed in a lying position, said body being aligned with said imaging and source means.

* * * * *